US 008084426B2

(12) United States Patent
Moore et al.

(10) Patent No.: US 8,084,426 B2
(45) Date of Patent: Dec. 27, 2011

(54) PHARMACEUTICAL COMPOSITION COMPRISING FGF18 AND IL-1 ANTAGONIST AND METHOD OF USE

(75) Inventors: Emma E. Moore, Seattle, WA (US); Jeff L. Ellsworth, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/784,377

(22) Filed: May 20, 2010

(65) Prior Publication Data

US 2010/0291212 A1   Nov. 18, 2010

Related U.S. Application Data

(60) Division of application No. 12/103,420, filed on Apr. 15, 2008, now Pat. No. 7,749,965, which is a continuation of application No. 11/175,734, filed on Jul. 6, 2005, now abandoned.

(60) Provisional application No. 60/585,655, filed on Jul. 6, 2004.

(51) Int. Cl.
*A61K 38/18* (2006.01)

(52) U.S. Cl. .................................................. 514/9.1

(58) Field of Classification Search ................ None
See application file for complete search history.

(56) References Cited

U.S. PATENT DOCUMENTS

| 6,352,971 | B1 | 3/2002 | Deisher et al. |
| 6,599,873 | B1 | 7/2003 | Sommer et al. |
| 6,733,753 | B2 | 5/2004 | Boone et al. |
| 7,067,144 | B2 | 6/2006 | Demopulos et al. |
| 7,745,138 | B2 * | 6/2010 | Whitehead ............. 435/455 |
| 7,749,965 | B2 | 7/2010 | Moore et al. |
| 2003/0199443 | A1 | 10/2003 | Deisher et al. |
| 2004/0136970 | A1 | 7/2004 | Ellsworth et al. |
| 2006/0009389 | A1 | 1/2006 | Moore et al. |
| 2008/0194472 | A1 | 8/2008 | Whitsett |

FOREIGN PATENT DOCUMENTS

| WO | WO 0139788 | 6/2001 |
| WO | WO 2004/022718 | 3/2004 |
| WO | WO 2004/032848 | 4/2004 |
| WO | WO 2004/032849 | 4/2004 |
| WO | WO 2004/047857 | 6/2004 |
| WO | WO 2006/014444 | 2/2006 |

OTHER PUBLICATIONS

Ellsworth J L et al., "Fibroblast Growth Factor-18 (FGF 18) Reduces Infarct Volume and Behavioral defecit After Occlusion of the Middle Cerebral Artery in Rats", BIOSIS, 2001, vol. 27, No. 2, p. 2026.

Ellsworth et al., "Fibroblast growth factor-18 is a trophic factor for mature chondrocytes and their progenitors", Osteoarthritis and Cartilage/OARSI, Osteoarthritis Research Society, Apr. 2002, vol. 10, No. 4, pp. 308-320.

Hu et al., "FGF-18, a novel member of the fibrblast growth factor family, stimulates hepatic and intestinal proliferation", Mollecular and Cellular Biology, Oct. 1998, vol. 18, No. 10, pp. 6063-6074.

* cited by examiner

*Primary Examiner* — Marianne P Allen
(74) *Attorney, Agent, or Firm* — Woodcock Washburn LLP (57) ABSTRACT

FGF18 is known to stimulate the proliferation of chondrocytes, bone, and nervous tissue, resulting in repair of diseased tissue. When an IL-1 antagonist is administered in addition to FGF18, the effects on the IL-1 mediated disease and also, the effect on cartilage, bone, and nervous cell proliferation, are found to be greater than administration of FGF18 or the IL-1 antagonist alone. The present invention encompasses a pharmaceutical composition that combines FGF18 with IL-1 antagonist and methods of treating IL-1 mediated disease using this pharmaceutical composition.

18 Claims, 1 Drawing Sheet

FIGURE 1

PHARMACEUTICAL COMPOSITION COMPRISING FGF18 AND IL-1 ANTAGONIST AND METHOD OF USE

REFERENCE TO RELATED INVENTIONS

This application is a divisional of U.S. application Ser. No. 12/103,420, filed on Apr. 15, 2008, now U.S. Pat. No. 7,749,965, issued on Jul. 6, 2010, which is a continuation of U.S. application Ser. No. 11/175,734, filed on Jul. 6, 2005, now abandoned, which claims the benefit of U.S. Provisional Application Ser. No. 60/585,655, filed Jul. 6, 2004, which is incorporated herein by reference.

BACKGROUND OF THE INVENTION

Interleukin-1α (IL-1α) and IL-1β are naturally occurring agonists of the type I IL-1 receptor (IL-1R$_I$). When either of these two molecules bind to the receptor, it activates and recruits a second receptor component, the IL-1R$_I$ accessory protein (AcP). The three-member complex (IL-1/Il-1R$_I$/AcP) initiates a signaling cascade that includes activation and nuclear translocation of the transcription factor NF-κB. This results in the expression of many cytokines and other proteins involved in inflammation and immune responses, causing or worsening many disease processes (Barnes, *Int. J. Biochem. Cell Biol.* 29:867-870, 1997). Particular diseases that are believed mediated by interleukin-1 include rheumatoid arthritis (RA) and osteoarthritis (OA) (Roshak et al., *Curr. Opin. Pharmacol.* 2(3): 316-21, 2002).

The body has evolved at least two methods of naturally inhibiting this pathway, the type II IL-1R (Il-1R$_{II}$), a so-called "decoy receptor," and the IL-1 receptor antagonist (IL-1ra). The decoy receptor can bind both IL-1α and IL-1β but does not initiate intracellular signaling (McMahan et al., *EMBO J.* 10: 2821-2832, 1991). Thus, it can pull agonist out of the system and block their biologic effects. IL-1ra binds to IL-1R$_I$ with high affinity but does not activate the receptor or cause a biological response. It therefore acts a competitive antagonist to IL-1α and IL-1β (Arend, *Prog. Growth Factor Res.* 2(4): 193-205, 1990). Genetically engineered antagonists, such as anti-Il-1R$_I$ antibodies (Fredricks et al., *Pro. Eng. Des. & Selec.* 17 (1): 95-106, 2004) and IL-1ra-Fc fusion proteins (U.S. Pat. No. 6,733,753) have also been developed.

Overexpression of proinflammatory cytokines like IL-1 has been shown to play a major role in the pathogenesis of immunoinflammatory diseases such as rheumatoid arthritis (RA), a common chronic autoimmune disorder characterized by inflammation of synovial tissues, joint swelling, stiffness and pain that may progress to joint destruction (Bingham, *J. Rheumatol.* 29: 3-9, 2002). The clinical application of antagonizing IL-1α and IL-1β in this disease has investigated with anakinra (Kineret®), a recombinant, non-glycoslyated from of human IL-1ra. The use of this therapeutic protein has led to a reduction in frequency and severity of joint damage in RA patients (Bresnihan, *Ann. Rheum.* 61, ii74-ii77, 2002 and St. Clair, *J. Rheumatol.* 29, 22-26, 2002), however the treatment does not appear to reverse already existing damage to the cartilage or bone of the affected joints.

The fibroblast growth factor (FGF) family consists of at least twenty-three distinct members which generally act as mitogens for a broad spectrum of cell types (Ornitz and Itoh, *Genom. Biol.* 2(3):reviews3005.1-3005.12, 2001). FGF18 was identified as a member of the FGF family that is most closely related to FGF8 and FGF17. Activities associated with FGF18 included stimulation of mesenchymal lineage cells, in particular cardiac myocytes, osteoblasts and chondrocytes (U.S. Pat. No. 6,352,971 and Ellsworth et al., *Osteoarthritis and Cartilage*, 10(4):308-320, 2002). FGF18 binds and activates FGFR4 and the "Mc" splice variants of FGFR3 and FGFR2 (Ellsworth et al. *Osteo Cartil.* 10: 208-320 (2002)). It has been shown that FGFR3-IIIc and FGFR2-IIIc play a role in bone development and growth and cartilage growth (Davidson et al. *J. Biol. Chem.* 280:20509-20515 (2005)). Mice made homozygous null for the FGFR3 (−/−) resulted in postnatal skeletal abnormalities (Colvin et al., Nature Genet. 12:309-397, 1996 and Deng et al., Cell 84:911-921, 1996). The mutant phenotype suggests that in normal mice, FGFR-3 plays a role in regulation of chondrocyte cell division in the growth plate region of the bone (Goldfarb, *Cytokine and Growth Factor Rev.* 7(4):311-325, 1996). FGFR-IIIc is expressed in early mesenchymal condensates and in the developing periosteum. FGFR 2-IIIc −/− mice exhibit delayed ossification, premature loss of bone growth in the skull and long bone (Eswarakumar et al. Development 129:3783-3793 (2002)). FGF receptor mutations are also found in human chondrodysplasia and craniosynostosis syndromes (Ornitz and Marie, *Genes and Dev.* 16: 1446-1465, 2002).

Bone remodeling is the dynamic process by which tissue mass and skeletal architecture are maintained. The process is a balance between bone resorption and bone formation, with two cell types thought to be the major players. These cells are the osteoblast and osteoclast. Osteoblasts synthesize and deposit matrix to become new bone. The activities of osteoblasts and osteoclasts are regulated by many factors, systemic and local, including growth factors. This function provides a potential role for growth factors, such as FGF18, in disease states requiring activation of bone remodeling, such as damage to bone occurring in inflammatory diseases of the joints such as RA or osteoarthritis (OA). Other therapeutic applications for growth factors influencing bone remodeling include, for example, the treatment of injuries which require the proliferation of osteoblasts to heal, such as fractures, as well as stimulation of mesenchymal cell proliferation and the synthesis of intramembraneous bone which have been indicated as aspects of fracture repair (Joyce et al. 36th Annual Meeting, Orthopaedic Research Society, Feb. 5-8, 1990. New Orleans, La.).

Replacement of damaged articular cartilage caused either by injury or disease is a major challenge for physicians, and available treatments are considered unpredictable and effective for only a limited time. Virtually all the currently available treatments for cartilage damage focus on relief of pain, with little or no emphasis on regeneration of damaged tissues. Therefore, the majority of younger patients either do not seek treatment or are counseled to postpone treatment for long as possible. When treatment is required, the standard procedure is a total joint replacement or microfracture, a procedure that involves penetration of the subchondral bone to stimulate fibrocartilage deposition by chondrocytes. While deposition of fibrocartilage is not a functional equivalent of articular cartilage, it is at the present the best available treatment because there has been little success in replacing articular cartilage. Two approaches to stimulating deposition of articular cartilage that are being investigated are: stimulating chondrocyte activity in vivo and ex vivo expansion of chondrocytes and their progenitors for transplantation (Jackson et al., *Arthroscopy: The J. of Arthroscopic and Related Surg.* 12:732-738, 1996). In addition, regeneration or repair of elastic cartilage is valuable for treating injuries and defects to ear and nose. Any growth factor with specificity for chondrocytes lineage cells that stimulates those cells to grow, differentiate or induce cartilage production would be valuable for maintaining, repairing or replacing articular cartilage. FGF18 appears to promote chondrogenesis and cartilage repair in osteoarthritis in rats (Moore et al. *Osteoarthritis and Cartilage*, 13:623-631 (2005)) and thus, may be useful for repairing damaged cartilage.

Thus, there exists a need in the art for a method of treating a disease, such as immunoinflammatory diseases mediated by interleukin-1, that involves both blocking the inflammatory action of IL-1 and the repair of cartilage and bone through stimulation of mesenchmally-derived cells such as chondrocytes, osteocytes, and nervous tissue and their progenitors.

SUMMARY OF THE INVENTION

The present invention encompasses a pharmaceutical composition for the treatment of interleukin-1 mediated disease in a patient comprising FGF18 and an IL-1 antagonist. The FGF18 can comprise amino acid sequence 28-207 or 196-207 of SEQ ID NO:2 or functionally active fragments thereof such as those C-terminally truncated at Met 175, or those comprising Tyr 55 to Met 175, Lys 196, or Ala 207 and variants. The IL-1 antagonist can be any molecule that blocks IL-1 biological function, but is preferably selected from the group consisting of IL-1ra, recombinantly engineered formulations of IL-1ra such as anakinera (Kineret®), an anti-IL-1R$_I$ antibody, and a fusion protein of IL-1ra or an IL-1 inhibitory fragment fused with a constant domain of a heavy or light chain of human immunoglobulin at the amino-terminus of said IL-1ra. The IL-1ra sequence can be SEQ ID NO:5 and the constant region can be from a heavy chain, such as human IgG.

The composition can further comprise a negatively charged carrier selected from the group consisting of low molecular weight hyaluronans, high molecular weight hyaluronans, sulfated proteoglycans, B-cyclodextrin tetradecasulphate, hydroxyapatite, polylactide matrices, polylactide-coglycolide, alginate microspheres, chitosans, and methylcellulose. The composition can also be a time-release formulation, such as those comprising a matrix which is a solution, a gel, a paste, or a putty and can include a reservoir system. The composition can further comprising an anti-inflammatory drug.

The present invention also contemplates a method for treatment of an interleukin-1 mediated disease in a patient in need of such treatment comprising the step of administering a pharmaceutical composition comprising FGF18 and an IL-1 antagonist. Although numerous methods of administration are contemplated, two that are preferred is intraarticular injection and surgical implantation. The method can also comprise the steps of allowing growth of new cartilage, bone, or nervous tissue and surgically contouring the new cartilage, bone or nervous surface. Although any interleukin-1 mediated disease can be treated using the presently claimed methods, two preferred diseases including rheumatoid arthritis and osteoarthritis.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "hyaluronic acid" are used herein to include derivatives of hyaluronic acid that include esters of hyaluronic acid, salts of hyaluronic acid and also includes the term hyaluronan. The designation also includes both low and high molecular weight forms of hyaluronans and crosslinked hyaluronans or hylans. Examples of such hyaluronans are Synvisc® (Genzyme Corp. Cambridge, Mass.), ORTHOVISC® (Anika Therapeutics, Woburn, Mass.), and HYALGAN® (Sanofi-Synthelabo Inc., Malvern, Pa.)

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

A disease or medical condition is considered to be an "interleukin-1 mediated disease" if the spontaneous or experimental disease or medical condition is associated with elevated levels of IL-1 in bodily fluids or tissue or if cells or tissues taken from the body produce elevated levels of IL-1 in culture. In many cases, such interleukin-1 mediated diseases are also recognized by the following additional two conditions: (1) pathological findings associated with the disease or medical condition can be mimicked experimentally in animals by the administration of IL-1; and (2) the pathology induced in experimental animal models of the disease or medical condition can be inhibited or abolished by treatment with agents which inhibit the action of IL-1. In most interleukin-1 mediated diseases at least two of the three conditions are met, and in many interleukin-1 mediated diseases all three conditions are met.

All references cited herein are incorporated by reference in their entirety.

The present invention is based in part on the discovery that when compositions of FGF18 polypeptides or proteins plus a IL-1 antagonist such as anakinera (Kineret®) or an anti-IL-1$R_I$, are administered to a patient suffering from an interleukin-1 mediated disease, the stimulatory effects of the FGF18 are enhanced and not only are disease symptoms reduced, but repair occurs to damaged cartilage, bone, or nervous tissues involved in the disease. Therefore, the present invention is directed to compositions of FGF18 polypeptides or proteins plus, in particular hyaluronic acid for stimulating the proliferation of mesenchymal cells, particularly chondrocytes, bone, and nerves. For stimulation of chondrocytes, the compositions can be administered intraarticularly to a joint.

The nucleotide sequence of the FGF18 cDNA is described in SEQ ID NO. 1, and its deduced amino acid sequence is described in SEQ ID NO. 2. FGF18 was originally designated zFGF5, and is fully described in commonly assigned U.S. Pat. Nos. 6,352,971 and 5,989,866, both incorporated herein by reference. Analysis of the cDNA encoding a FGF18 polypeptide (SEQ ID NO: 1) revealed an open reading frame encoding 207 amino acids (SEQ ID NO: 2) comprising a mature polypeptide of 180 amino acids (residue 28 to residue 207 of SEQ ID NO: 2). Additionally, when human FGF18 is produced in bacterial expression systems it is common for amino acids from the carboxy terminus to be truncated. Examples of truncation include at Met 175 or Lys 196. Tests have revealed that these truncated fragments that have equivalent, if not superior, mitogenic activity on meschymally derived cells, such as primary articular chondrocytes. Furthermore, in animal models, the truncated fragments have not exhibited any heightened antigenic tendencies.

The mouse FGF18 polynucleotide sequence as shown in SEQ ID NO: 3 and corresponding amino acid sequence as shown in SEQ ID NO: 4 were found to have a high degree of homology to that of the human ortholog. At the amino acid level, the mouse and human polypeptides are approximately 98% identical, with three amino acid changes. Those skilled in the art will recognize that the sequences disclosed in SEQ ID NO: 1 or SEQ ID NO: 3 and SEQ ID NO: 2 and SEQ ID NO: 4 represent a single allele of the human and mouse FGF18 gene and polypeptide, respectively, and that allelic variation and alternative splicing are expected to occur.

Members of the FGF family are characterized by heparin binding domains. A putative heparin-binding domain for FGF18 has been identified in the region of amino acid residue 148 (Gly) to amino acid residue 169 (Gln) of SEQ ID NO: 2 and SEQ ID NO: 4. It is postulated that receptor-mediated signaling is initiated upon binding of FGF ligand complexed with cell-surface heparin sulfate proteoglycans. Many FGF family members can be placed into one of two related families on the basis of their structures and functions. aFGF and bFGF consist of three exons separated by two introns of variable length. FGF-8 consists of five exons, the first three of which correspond to the first exon of aFGF and bFGF. All the known FGF family members are spliced to form single polypeptides.

Analysis of the ligand-receptor complex of FGF18 has demonstrated that FGF18 has specificity for FGFR4 and the "Inc" splice variants of FGFR3 and FGFR2. FGFR3-IIIc and FGFR2-IIIc have been identified within chondrocytes of cartilage tissue, and in particular, both receptors have been found within human articular cartilage. FGFR3 and FGFR2 have been found in the growth plate of mammals and play important roles in the formation of endochondral and intramembranous bone. In particular, FGFR2 and FGFR3 play important roles in developing endochondral and intramembranous bone, FGFR2 is first expressed in condensing mesenchyme and FGFR3 expression is initiated as chondrocytes differentiate and proliferate. In developing cranial bones, FGFR3 is found in the dura mater and periosteum, whereas FGFR2 is expressed in osteoprogenitor cells at the osteogenic front separating the sutures. FGFR2 is also expressed in traebecular bone. (Ornitz and Marie, ibid., 2002) Previously, it has been shown that FGF18 is a proliferative agent for chondrocytes and osteoblasts, depending upon both the differentiated state of these cell types and the mode of administration. (See, U.S. Pat. Nos. 6,352,971 and 5,989,866; Ellsworth et al. *Osteoarthritis and Cartilage,* 10:308-320, 2002; Shimoaka et al., *J. Bio. Chem.* 277 (9) 7493-500, 2002). FGF18 has also been shown to facilitate cartilage repair in a rat model of osteoarthritis (Moore et al. *Osteoarthritis and Cartilage,* 13: 623-631 (2005)).

In order to be more effective in treating interleukin-1 mediated disease, the FGF18 molecules described above can be combined with IL-1 antagonists to provide pharmaceutical compositions that not only block the inflammatory and immunomodulatory effects of IL-1 but also provide proliferative effects upon the cartilage, bone, and/or nerve cells damaged during the disease state.

An "IL-1 antagonist" for the purposes of the present invention comprises any molecule that blocks the action of IL-1α and/or IL-1β by whatever method, including blocking the binding of these agonists to the IL-1R receptor or the blocking of the signal transduction effect of the receptor itself. Thus, IL-1$R_I$ antagonists and Il-1$R_{II}$ are included in the general definition of IL-1 antagonists. Some non-limiting examples of IL-1 antagonists include the monocyte-derived inhibitor described in U.S. Pat. No. 5,075,222; secreted (sIL-1ra) and intracellular (icIL-1ra) forms of the interleukin-1 receptor antagonist described in C. Butcher et al., *J. Immunol.,* 153: 701-711, 1994; a second intracellular form (icIL-1raII) described in U.S. Pat. Nos. 5,739,282; 5,837,495; and 5,981, 713; the IL-1 inhibitor described in U.S. Pat. No. 5,359,032; the IL-1ra described in U.S. Pat. No. 5,455,330; the IL-1 antagonist described in U.S. Patent No. and the interleukin-1 inhibitors and methods described in U.S. Pat. Nos. 6,096,728; 6,159,460; 6,294,170; and 6,599,873. It also includes the molecules described in U.S. Application No. 20030166069. IL-1 antagonists also include antibodies that interfere with the interactions between IL-1 and its receptors in a way to alter its biological function. Methods of producing such antibodies can be found in Fredericks et al., referenced supra, and in U.S. Application Nos. 20040097712 and 20030026806. It is anticipated that the anti-IL-1$R_I$ antibodies described by Fredericks et al. may undergo affinity maturation as well known in the art (for example, Yang et al., *J. Mol. Biol.* 254:392-403, 1995).

The present invention can be used to treat any disease believed to be interleukin-1 mediated as defined above or as understood by one of ordinary skill in the art. A non-exclusive list of acute and chronic interleukin-1 (IL-1)-mediated inflammatory diseases includes but is not limited to the following: acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemohorragic shock; hyperalgesia, inflammatory bowel disease; inflammatory conditions of a joint, including osteoarthritis, psoriatic arthritis and rheumatoid arthritis; degenerative disk disease; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

As osteoarthritis causes pain in the joints, thought to be caused by a deficiency in the production of extracellular matrix including sulfated proteoglycans, hyaluronic acid (HA) and type II collagen, the present pharmaceutical composition may also include a negatively charged carrier such as HA. HA is natural high viscosity mucopolysaccharide with alternating, (1-3) glucuronidic and, (1-4) glucosaminidic bonds. It is found in the umbilical cord, in vitreous humor, and synovial fluids. For use in the treatment methods and compositions of the present invention, any source of HA is appropriate, however, recombinantly-produced HA (i.e., protein produced in bacterial, yeast, or mammalian cell culture) may be preferred over isolation from animal or human tissue sources in order to insure purity of the composition. In the connective tissue HA functions as binding and protective agent. HA fractions and salts of HA have been used for treatment of damaged bone joints and osteoarthritis. (See, U.S. Pat. Nos. 5,925,626; 5,631,241 and EP 0,939,086.) HA is also used in viscosuregery and viscoupplementation and as an aid in ophthalmic surgery.

HA has been used as a component for therapeutic treatment of a variety conditions, both using the HA as the primary therapeutic and as a component of a therapeutic composition useful for treatment. In experiments done by others, HA scaffolds were used to implant autologous chondrocytes into patients' knees, with data showing that symptomatic and functional improvements results. Raynauld et al. (*Osteoarthritis and Cartilage,* 10(7):506-517, 2002) describe results using an HA formulation in conjunction with appropriate care in which clinically effectiveness for primary and secondary outcomes were improved over appropriate care alone. Generally, primary outcomes can be measured as change in the Western Ontario and McMaster (WOMAC) osteoarthritis index, which is a measurement of pain. Secondary outcomes measures will include functional disability and self-reported quality of life. If the therapeutic outcome includes a disease modifying agent, then joint morphology is a primary outcome variable, as well. (Hochberg et al., *J. of Rhematolog.* 24(4): 792-794, 1997).

U.S. Pat. No. 4,636,524 discloses cross-linked gels of HA, alone and mixed with other hydrophilic polymers and containing various substances or covalently bonded low molecular weight substances and processes for preparing them. These products are useful in numerous applications including cosmetic formulations and as drug delivery systems. HA is known to be a biologically tolerable polymer in the sense that it does not cause any immune or other kind of response when introduced into a human body, the cross-linked HA gels can be used for various medical applications. The cross-linked gels modified with other polymers or low molecular weight substances can be used as drug delivery devices.

Canadian Letters Patent 1,240,929 teaches the combination of chondroitin sulfate compound and a hyaluronate to protect both human and animal cell layers and tissue subject to exposure to trauma.

U.S. Pat. No. 4,851,521 and European Patent Application 0,265,116, both describe HA fractions and cross-linked esters of HA. U.S. Pat. No. 4,851,521 describes esters of HA incorporated into pharmaceutical preparations as the active ingredient and as vehicles for ophthamological medicines for topical use and in suppositories for a systemic effect due to the effect of transcutaneous absorption, such as in suppositories.

U.S. Pat. Nos. 6,221,854 and 5,942,499 C1 (Reexam 4806) describe the use of HA and basic FGF (FGF-2) for the treatment of bone. The patent teaches an injectable mixture that is administered into an orthotopic or intraosseous site of desired bone growth.

In contrast, the combination of FGF18 polypeptide, IL-1 antagonist, and HA compositions of the present invention provides a composition and method that includes the stimulation and proliferation of mature chondrocytes and/or their progenitors, in particular differentiated chondrocytes, capable of inducing specialized cell functions, normally associated with terminally differentiated cells. When the composition of the present method is administered locally to articular cartilage, proliferation of the cells and concomitant synthesis of glycosaminoglycans is increased beyond the results seen with FGF18 alone, IL-1 antagonist alone, or HA alone. These results indicate that composition of the present method can play a therapeutic role in maintaining or repairing cartilaginous tissue, such as joints damaged by osteoarthritis, rheumatoid arthritis or traumatic injury.

FGF18 has been shown to increase cartilage deposition both in vivo and in vitro. Generation of hyaline cartilage, elastic cartilage, and fibrocartilage are valuable both as a therapeutic and as component for biological matrices. FGF18 and IL-1 antagonists (either with or without HA) compositions will be useful in treating articular cartilage defects in synovial joints that are due to age-related superficial fibrillation, cartilage degeneration due to osteoarthritis, and focal chondral and osteochondral defects due to injury or disease. FGF18, IL-1 antagonist (either with or without HA) compositions will also be useful for treating joint disease caused by osteochondritis dissecans and degenerative joint disease. In the field of reconstructive and plastic surgery, FGF18 and IL-1 antagonists (either with or without HA) compositions will be useful for autogenous or allogenic cartilage expansion and transfer for reconstruction of extensive tissue defects. Expansions of cells and induction of elastic cartilage production will be useful for generation and repair of ear and nose tissue.

FGF18 and IL-1 antagonist compositions can administered by any means, either systemically or locally, known to one of ordinary skill in the art such as subcutaneous, intraperitoneal, or by intravenous administration. Depending on the disease being treated, one preferred method may be application by direct injection into the synovial fluid of the joint or directly into the defect, either alone or complexed with a suitable carrier for extended release of protein. However, when FGF18, IL-1 antagonist, and HA is delivered directly to the synovial joint, the effects of the compositions to stimulate chondrocytes proliferation exceeds that of FGF18 polypeptide, IL-1 antagonist, or HA alone.

FGF18 can also be used to expand chondrocyte, bone, or nervous tissue populations in culture for autogenous or allogenic transplantation and then administered with concurrent treatment consisting of administration of FGF18 polypeptide and IL-1 antagonist compositions. In these procedures, for example, chondrocytes can be harvested arthroscopically from an uninjured minor load-bearing area of the damaged joint, and can be cultured in the presence of FGF18 compositions to increase the number of cells prior to transplantation. The expanded cultures will then be admixed with FGF18 polypeptide and IL-1 antagonist compositions, and placed in the joint space or directly into the defect. FGF18 and IL-1 antagonist compositions can be used in combination with periosteal or perichondrial grafts that contain cells that can form cartilage and/or help to hold the transplanted chondrocytes or their precursor cells in place. FGF18 and IL-1 antagonist compositions can be used to repair cartilage damage in conjunction with lavage of the joint, stimulation of bone marrow, abrasion arthroplasty, subchondral drilling, or microfracture of the subchondral bone. Additionally, after the growth of cartilage due to the administration of the FGF18 and IL-1 antagonist composition, additional surgical treatment may be necessary to suitably contour the newly formed cartilage, bone, or nervous tissue surface.

The compositions of the present invention provide a method for stimulating chondrocyte proliferation and cartilage production in cartilagenous tissues that have been damaged due to traumatic injury or chondropathy. Of particular importance for treatment are tissues that exhibit articulated surfaces, such as, spine, shoulder, elbow, wrist, joints of the fingers, hip, knee, ankle, and the joints of the feet. Examples of diseases that may benefit from treatment include osteoarthritis, rheumatoid arthritis, other autoimmune diseases, or osteochondritis dessicans. In addition, cartilage malformation is often seen in forms of dwarfism in humans suggesting that FGF18 would be useful in these patients.

FGF18 and IL-1 antagonist compositions can be applied by direct injection into the synovial space of the joint, into nearby tissues, or directly into a cartilage defect in combination with a carrier that exhibits a negative charge under physiological conditions. Since FGF18 has an isoelectric point of >9.0, at physiological pH FGF18 exhibits a net positive charge. Thus carrier molecules with an abundance of negative charge may bind FGF18 and enhance its activity. Such carriers include low and high molecular weight hyaluronans, sulfated proteoglycans, polylactide matrices, polylactide-co-glycolides, B-cyclodextrin tetradecasulphate, hydroxyapatite, alginate microspheres, chitosans, methylcellulose, and other polymers well known in the art.

For pharmaceutical use, the compositions of the present invention are formulated for intraarticular administration according to conventional methods. The dosage regiment will be determined using various patient variables (e.g., weight, age, sex), as well as clinical presentation (e.g., extent of injury, site of injury, etc.) In general, pharmaceutical formulations will include a FGF18 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, extend half-life, etc. The FGF18 and IL-1 antagonist may be administered separately or in combination as a single composition. Thus, the formulations may be provided as a single formulation or as a multicomponent kit. Methods of formulation are well known in the art and are disclosed, for example, in *Remington's Pharmaceutical Sciences*, Gennaro, ed., Mack Publishing Co., Easton Pa., 1990, which is incorporated herein by reference. Determination of dose is within the level of ordinary skill in the art. The proteins may be administered for acute treatment, over one week or less, often over a period of one to three days or may be used in chronic treatment, over several months or years.

Administration of proteins generally requires a formulation that prolongs the half-life or biological activity of the active protein by increasing the resistance to proteolytic degradation or aggregation. Delivery of a protein therapeutic composition can also be difficult when the site for therapeutic action is preferably limited to a specific location in the body. The present invention provides formulations of FGF18 and IL-1 antagonist that will be easier to administer and more effective, and other uses that should be apparent to those skilled in the art from the teachings herein.

In other embodiments, a pharmaceutical FGF18 and IL-1 antagonist composition will comprise a formulation for timed-release of the protein. Time-release formulations generally include a monolithic delivery device comprising biocompatible solutions, gels, pastes, and putties in a matrix, in which the composition is entrapped or dissolved. Release from such a timed-release composition occurs by diffusion through the matrix and/or erosion of the matrix. A reservoir system, where the pharmaceutical composition diffuses through a membrane, may also be used.

Although administration of FGF18 and IL-1 antagonists in a pharmaceutically acceptable admixture, is sufficient to provide the treatment method of the present invention there may be clinical situations where additional drugs are combined in the admixture. Examples of other drugs which may be clinically indicated include anti-inflammatory drugs such as non-specific and specific cyclooxygenase-2 inhibitors, non-steriodal and steroidal anti-inflammatory drugs. Some of the nonspecific COX inhibitors that could be used in the present invention include salicylic acid and derivatives, such as aspirin or sulfasalazine, para-aminophenol derivatives, such as acetaminophen, indole and indene acetic acids, such as indomethacin or sulindac, arylpropionic acids, such as ibuprofen, naproxen, or oxaprozin, anthranilic acids, such as mefenamic acid, enolic acids including oxicams, or alkanonoes, such as nabumentone. Specific COX-2 inhibitors would be diaryl-substituted fuanonoes (Refecoxib), diaryl-substituted pyrazoles (Celecoxib), indole acetic acids (Etodolac) and sulfonaildes (Nimesulide). Additionally, steroids, such as dexamethazone, prednisone, triamcinolone, or methylprednisone, are among the drugs that could be used. Other types of drugs suitable for the present invention would be inhibitors of the tumor necrosis factor family, such as Enbrel or TACI-Ig, antagonists of IL-18 and IL-15, and immunosuppressive drugs such as cyclosporine. In addition, FGF18 may be administered with inhibitors of the CC (MCP-1, RANTES, MIP-1alpha, and MIP-1beta) and CXC (IL-8 and GRO-alpha) chemokine family.

The invention is further illustrated by the following non-limiting examples.

EXAMPLE 1

The Effect of IL-1β on the Mitogenic Activity of FGF18

Isolation of Normal Human Articular Chondrocytes

Normal human chondrocytes were isolated from the talus bone obtained from the North West Tissue Center (Seattle, Wash.). Samples were digested overnight in collagenase (Worthington Type II; 1 mg/ml) and plated the next day in serum-free DMEM/F12 containing ITS (insulin/transferring/selenium), glutamine, pyruvate, Hepes (25 mM), and ascorbic acid (50 µg/ml). The majority of the cells displayed a rounded morphology characteristic of well-differentiated chondrocytes and >90% of the cells expressed type II collagen, characteristic of well-differentiated chondrocytes. All assays were performed on first passage cells.

Mitogenic Assay (3H-thymidine uptake)

Chondrocytes obtained from normal individuals were plated in 96-well plates at a density of 30,000 cells per 96-well in either serum-free medium or serum-free medium containing 1% serum. After 4 days, the media was changed to serum-free media containing 0.1% BSA. In both cases, the chondrocytes retained their well-differentiated, rounded, morphology. FGF18 was added to the wells after an additional 48 hrs of culture and $^3$H-thymidine (2 µC/ml) was added 48 hrs later. Fetal calf serum (10%) was used as a positive control. After an additional 24 hrs, the cells were harvested with a solution of trypsin and collagenase type II (2 mg/ml, Worthington) and counted to determine the number of incorporated cpm.

Figure 1:
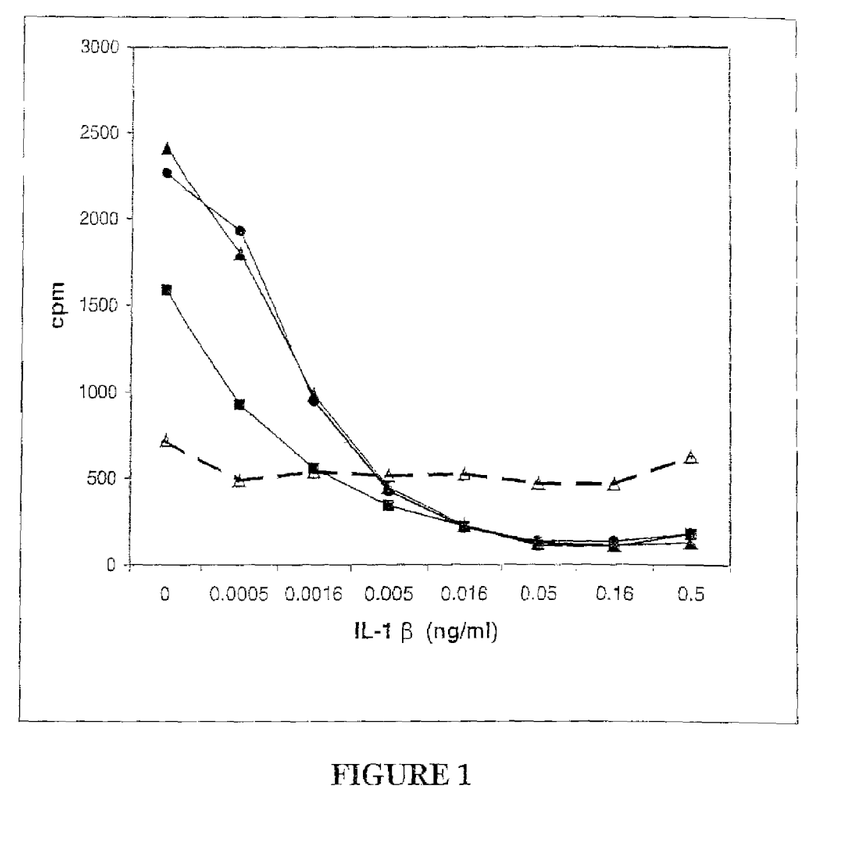
FIG. 1 graphically represents the effect of IL-1β on the mitogenic activity of FGF18. In the graph, 5 ng/ml FGF18 is represented by the closed squares, 50 ng/ml is represented by closed circles; 500 ng/ml is represented by closed triangles; and IL-1β is represented by open triangles.

Studies were also performed to assess the effect of IL-1β therein; on the mitogenic activity of FGF18. For these assays, chondrocytes were plated in serum-free medium and FGF18 and/or human IL-1□ were added after 48 hrs. $^3$H-thymidine (2 µC/ml) was added 48 hrs later and the cells harvested and counted after 24 hrs. The results of this experiment are graphically represented in FIG. 1. This experiment indicates IL-1 partially suppresses the proliferative effect of FGF18, so that inhibition of IL-1 activity will benefit the proliferative effect of FGF18 on meschymally derived cells, such as chondrocytes.

EXAMPLE 2

Intraarticular Injection of FGF18 and IL-1 Antagonist

FGF18 is lyophilized and reconstituted at the appropriate concentration in either PBS or 0.5% hyaluronan (0.2 um sterile filtered). A single dose of FGF18, vehicle PBS or hyaluronan, or the appropriate combination of FGF18 dissolved in either PBS and hyaluronan and IL-1 antagonist, contained in a final volume of 5 µl is injected into the intraarticular space of the left stifle (knee) of 10 week old female c57/B16 mice. All dosing is performed under isoflurane anesthesia and 100 µl of buprenorephine is administered upon recovery for analgesia. The animals are sacrificed 2 weeks after dosing and tissues are taken for routine histology.

The following dose groups were used:

| Group | treatment |
|---|---|
| 1 | no treatment |
| 2 | PBS |
| 3 | 5 μg FGF18 in PBS + IL-1 antagonist |
| 4 | 0.5 μg FGF18 in PBS + IL-1 antagonist |
| 5 | 0.05 μg FGF18 in PBS + IL-1 antagonist |
| 6 | hyaluronan 0.5% |
| 7 | hyaluronan 0.5% + 5.0 μg FGF18 + IL-1 antagonist |
| 8 | hyaluronan 0.5% + 0.5 μg FGF18 + IL-1 antagonist |
| 9 | hyaluronan 0.5% + 0.05 μg FGF18 + IL-1 antagonist |
| 10 | sham injection |

EXAMPLE 3

Treatment of RA Model

1. Rat Adjuvant Arthritis

Rats are prepared as described in Benedele et al., *Arth. Rheum.* 42(3):498-506, 1999. Briefly, male rats are given single subcutaneous (SC) injections of 100 microliters of CFA to which 5 mg/ml of lipoidalamine (LA) was added. Treatments were initiated on day 8, which was 1-2 days prior to the onset of arthritis.

Rats are treated with varying concentrations of FGF18 and IL-1 antagonist, both alone and in combination and preferably both with and without HA carrier through intra-articular injection. Paw weight, ankle joint diameter, and area under the curve for ankle joint diameter are among the variables measured after treatment. Additionally, histologic evaluation of inflammation, pannus formation, cartilage damage, and bone lesions is undertaken.

2. Rat Type II Collagen-Induced Arthritis

Rats are prepared as described in Benedele et al., *Arth. Rheum.* 42(3):498-506, 1999. Briefly, female rats are given intradermal/SC injections of bovine type II collagen (2 mg/ml in IFA) at the base of the tail and in three sites over the back on day 0 and day 7. On day 12 they are given an intraperitoneal injection of endotoxin (3 mg/kg). Onset of arthritis occurs over the next 5 days. As rats develop the disease, they are randomized to study groups and treatment is initiated on the first day that clinical signs of arthritis are clearly visible.

Rats are treated with varying concentrations of FGF18 and IL-1 antagonist, both alone and in combination and preferably both with and without HA carrier through intra-articular injection. Paw weight, ankle joint diameter, and area under the curve for ankle joint diameter are among the variables measured after treatment. Additionally, histologic evaluation of inflammation, pannus formation, cartilage damage, and bone lesions is undertaken.

EXAMPLE 4

Treatment of Osteoarthritis Model

To evaluate whether the combination of FGF18 and IL-1 antagonist could be more effective than FGF18 alone in generating chondral tissue and reversing cartilage degeneration in a setting of osteoarthritis (OA), OA is induced by creating a meniscal tear in the knee joint of rats. In this model, damage to the meniscus induces progressive cartilage degeneration and osteophyte formation that mimic the changes that occur in spontaneous osteoarthritis.

FGF18 is dissolved in a hyaluronan carrier, mixed with IL-1 antagonist and applied to the operated knee by intra-articular injection. The repair of cartilage degeneration is evaluated 3 weeks later. The medial collateral ligament of each rat is transected and the medial meniscus cut through the full thickness to simulate a complete tear. Three weeks after surgery, rats receive intra-articular injections of either vehicle (0.5% hyaluronan) or vehicle containing *E. coli*-derived recombinant human FGF18 (0.1, 1.0, or 5.0 ug) or FGF18 combined with IL-1 antagonist twice per week for three weeks. Four days after the last injection, the knee joints are harvested, collected into buffered formalin, decalcified, and embedded in paraffin for histology. Frontal sections of the knee joints are stained with toluidine blue to assess formation of chondral tissue. An image of the tibial plateau of each knee is captured using an Optimas image analysis system. Multiple sections of the right knee are analyzed microscopically and scored subjectively for cartilage degeneration (chondrocyte/matrix loss and fibrillation) and chondrophyte formation. Strict attention to zones (outside, middle, and inside thirds of the medial tibial plateau) are adhered to and summed to reflect total severity of tibial degeneration. Micrometer measurements of the total extent of the tibial plateau affected by degeneration, width of tibial lesions that extended >50% of cartilage thickness (Tibial Cartilage Degeneration Width), lesion depth (Depth Ratio), thickness of the medial tibial cartilage to the tidemark, and chondrophyte size and number are assessed. Statistical analysis of histopathologic parameters is done by comparing group means using the two-tailed Student's t-test or by analysis of variance. All injections and scoring are performed by investigators blinded to the treatment groups.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A pharmaceutical composition comprising FGF18 and an IL-1 antagonist, wherein the IL-1 antagonist is selected from the group consisting of (a) an IL-1ra and (b) a fusion protein comprising IL-1ra or an IL-1 inhibitory fragment fused with a constant domain of a heavy or light chain of human immunoglobulin.

2. The composition of claim 1 wherein the IL-1ra is recombinantly engineered.

3. The composition of claim 2 wherein the FGF18 comprises residue 28 to residue 207 of SEQ ID NO:2.

4. The composition of claim 2 wherein the FGF18 comprises residue 28 to residue 196 of SEQ ID NO:2.

5. The composition of claim 2 wherein the recombinantly engineered formulation of IL-1ra is anakinra.

6. The composition of claim 2 further comprising a negatively charged carrier selected from the group consisting of low molecular weight hyaluronans, high molecular weight hyaluronans, sulfated proteoglycans, polylactide matrices or polylactide-co-glycolide, B-cyclodextrin tetradecasulphate, hydroxyapatite, alginate microspheres, chitosans, and methylcellulose.

7. The composition of claim 2 wherein said composition is a time-release formulation.

8. The composition of claim 7 wherein said time-release formulation comprises a matrix selected from the group consisting of a solution, a gel, a paste, or a putty.

9. The composition of claim 7 wherein said time-release formulation comprises a reservoir system.

10. The composition of claim 2 further comprising an anti-inflammatory drug.

11. The composition of claim 1 wherein the IL-1 antagonist is a fusion protein comprising IL-1ra or an IL-1 inhibitory fragment fused with a constant domain of a heavy or light chain of human immunoglobulin.

12. The composition of claim 11 wherein the constant domain is a heavy chain.

13. The composition of claim 11 wherein the FGF18 comprises residue 28 to residue 196 of SEQ ID NO:2.

14. The composition of claim 11 wherein the FGF18 comprises residue 28 to residue 207 of SEQ ID. NO:2.

15. The composition of claim 11 further comprising a negatively charged carrier selected from the group consisting of low molecular weight hyaluronans, high molecular weight hyaluronans, sulfated proteoglycans, polylactide matrices or polylactide-co-glycolide, B-cyclodextrin tetradecasulphate, hydroxyapatite, alginate microspheres, chitosans, and methylcellulose.

16. The composition of claim 11 wherein said composition is a time-release formulation.

17. The composition of claim 16 wherein said time-release formulation comprises a matrix selected from the group consisting of a solution, a gel, a paste, or a putty.

18. The composition of claim 11 further comprising an anti-inflammatory drug.

* * * * *

SEQUENCE LISTING

<160> NUMBER OF SEQ ID NOS: 5

<210> SEQ ID NO 1
<211> LENGTH: 917
<212> TYPE: DNA
<213> ORGANISM: Homo sapiens
<220> FEATURE:
<221> NAME/KEY: CDS
<222> LOCATION: (1)...(621)

<400> SEQUENCE: 1

```
atg tat tca gcg ccc tcc gcc tgc act tgc ctg tgt tta cac ttc ctg      48
Met Tyr Ser Ala Pro Ser Ala Cys Thr Cys Leu Cys Leu His Phe Leu
 1               5                  10                  15 ctg ctg tgc ttc cag gta cag gtg ctg gtt gcc gag gag aac gtg gac      96
Leu Leu Cys Phe Gln Val Gln Val Leu Val Ala Glu Glu Asn Val Asp
            20                  25                  30 ttc cgc atc cac gtg gag aac cag acg cgg gct cgg gac gat gtg agc     144
Phe Arg Ile His Val Glu Asn Gln Thr Arg Ala Arg Asp Asp Val Ser
         35                  40                  45 cgt aag cag ctg cgg ctg tac cag ctc tac agc cgg acc agt ggg aaa     192
Arg Lys Gln Leu Arg Leu Tyr Gln Leu Tyr Ser Arg Thr Ser Gly Lys
 50                  55                  60 cac atc cag gtc ctg ggc cgc agg atc agt gcc cgc ggc gag gat ggg     240
His Ile Gln Val Leu Gly Arg Arg Ile Ser Ala Arg Gly Glu Asp Gly
 65                  70                  75                  80 gac aag tat gcc cag ctc cta gtg gag aca gac acc ttc ggt agt caa     288
Asp Lys Tyr Ala Gln Leu Leu Val Glu Thr Asp Thr Phe Gly Ser Gln
                 85                  90                  95 gtc cgg atc aag ggc aag gag acg gaa ttc tac ctg tgc atg aac cgc     336
Val Arg Ile Lys Gly Lys Glu Thr Glu Phe Tyr Leu Cys Met Asn Arg
            100                 105                 110 aaa ggc aag ctc gtg ggg aag ccc gat ggc acc agc aag gag tgt gtg     384
Lys Gly Lys Leu Val Gly Lys Pro Asp Gly Thr Ser Lys Glu Cys Val
         115                 120                 125 ttc atc gag aag gtt ctg gag aac aac tac acg gcc ctg atg tcg gct     432
Phe Ile Glu Lys Val Leu Glu Asn Asn Tyr Thr Ala Leu Met Ser Ala
 130                 135                 140 aag tac tcc ggc tgg tac gtg ggc ttc acc aag aag ggg cgg ccg cgg     480
Lys Tyr Ser Gly Trp Tyr Val Gly Phe Thr Lys Lys Gly Arg Pro Arg
145                 150                 155                 160 aag ggc ccc aag acc cgg gag aac cag cag gac gtg cat ttc atg aag     528
Lys Gly Pro Lys Thr Arg Glu Asn Gln Gln Asp Val His Phe Met Lys
                 165                 170                 175 cgc tac ccc aag ggg cag ccg gag ctt cag aag ccc ttc aag tac acg     576
Arg Tyr Pro Lys Gly Gln Pro Glu Leu Gln Lys Pro Phe Lys Tyr Thr
            180                 185                 190 acg gtg acc aag agg tcc cgt cgg atc cgg ccc aca cac cct gcc          621
Thr Val Thr Lys Arg Ser Arg Arg Ile Arg Pro Thr His Pro Ala
         195                 200                 205 taggccaccc cgccgcggcc ctcaggtcgc cctggccaca ctcacactcc cagaaaactg    681
catcagagga atattttac atgaaaaata aggattttat tgttgacttg aaaccccga     741 tgacaaaaga ctcacgcaaa gggactgtag tcaacccaca ggtgcttgtc tctctctagg    801
aacagacaac tctaaactcg tccccagagg aggacttgaa tgaggaaacc aacactttga    861
gaaaccaaag tccttttttcc caaaggttct gaaaaaaaaa aaaaaaaaaa ctcgag        917
```

<210> SEQ ID NO 2
<211> LENGTH: 207
<212> TYPE: PRT
<213> ORGANISM: Homo sapiens

<400> SEQUENCE: 2

```
Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
         35                  40                  45
```

```
Arg Lys Gln Leu Arg Leu Tyr Gln Leu Tyr Ser Arg Thr Ser Gly Lys
     50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
                100                 105                 110

Lys Gly Lys Leu Val Gly Lys Pro Asp Gly Thr Ser Lys Glu Cys Val
            115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
                180                 185                 190

Thr Val Thr Lys Arg Ser Arg Ile Arg Pro Thr His Pro Ala
                195                 200                 205

<210> SEQ ID NO 3
<211> LENGTH: 1023
<212> TYPE: DNA
<213> ORGANISM: Mus musculus
<220> FEATURE:
<221> NAME/KEY: CDS
<222> LOCATION: (1)...(624)

<400> SEQUENCE: 3 atg tat tca gcg ccc tcc gcc tgc act tgc ctg tgt tta cac ttt cta      48
Met Tyr Ser Ala Pro Ser Ala Cys Thr Cys Leu Cys Leu His Phe Leu
 1               5                  10                  15 ctg ctg tgc ttc cag gtt cag gtg ttg gca gcc gag gag aat gtg gac      96
Leu Leu Cys Phe Gln Val Gln Val Leu Ala Ala Glu Glu Asn Val Asp
                 20                  25                  30 ttc cgc atc cac gtg gag aac cag acg cgg gct cga gat gat gtg agt     144
Phe Arg Ile His Val Glu Asn Gln Thr Arg Ala Arg Asp Asp Val Ser
             35                  40                  45 cgg aag cag ctg cgc ttg tac cag ctc tat agc agg acc agt ggg aag     192
Arg Lys Gln Leu Arg Leu Tyr Gln Leu Tyr Ser Arg Thr Ser Gly Lys
     50                  55                  60 cac att caa gtc ctg ggc cgt agg atc agt gcc cgt ggc gag gac ggg     240
His Ile Gln Val Leu Gly Arg Arg Ile Ser Ala Arg Gly Glu Asp Gly
 65                  70                  75                  80 gac aag tat gcc cag ctc cta gtg gag aca gat acc ttc ggg agt caa     288
Asp Lys Tyr Ala Gln Leu Leu Val Glu Thr Asp Thr Phe Gly Ser Gln
                 85                  90                  95 gtc cgg atc aag ggc aag gag aca gaa ttc tac ctg tgt atg aac cga     336
Val Arg Ile Lys Gly Lys Glu Thr Glu Phe Tyr Leu Cys Met Asn Arg
                100                 105                 110 aaa ggc aag ctc gtg ggg aag cct gat ggt act agc aag gag tgc gtg     384
Lys Gly Lys Leu Val Gly Lys Pro Asp Gly Thr Ser Lys Glu Cys Val
            115                 120                 125 ttc att gag aag gtt ctg gaa aac aac tac acg gcc ctg atg tct gcc     432
Phe Ile Glu Lys Val Leu Glu Asn Asn Tyr Thr Ala Leu Met Ser Ala
130                 135                 140 aag tac tct ggt tgg tat gtg ggc ttc acc aag aag ggg cgg cct cgc     480
Lys Tyr Ser Gly Trp Tyr Val Gly Phe Thr Lys Lys Gly Arg Pro Arg
```

```
                    145                 150                 155                 160
aag ggt ccc aag acc cgc gag aac cag caa gat gta cac ttc atg aag                  528
Lys Gly Pro Lys Thr Arg Glu Asn Gln Gln Asp Val His Phe Met Lys
                    165                 170                 175 cgt tac ccc aag gga cag gcc gag ctg cag aag ccc ttc aaa tac acc                  576
Arg Tyr Pro Lys Gly Gln Ala Glu Leu Gln Lys Pro Phe Lys Tyr Thr
            180                 185                 190 aca gtc acc aag cga tcc cgg cgg atc cgc ccc act cac ccc ggc tag                  624
Thr Val Thr Lys Arg Ser Arg Arg Ile Arg Pro Thr His Pro Gly *
        195                 200                 205 gtccggccac actcacccccc ccagagaact acatcagagg aatattttta catgaaaaat               684
aaggaagaat ctctattttt gtacattgtg tttaaaagaa gacaaaaact gaacctaaag                744
tcttgggagg aggggcgata ggattccact gttgacctga accccatgac aaaggactca                804
cacaagggga ccgctgtcaa cccacaggtg cttgcctctc tctaggaggt gacaattcaa                864
aactcatccc cagaggagga cttgaacgag gaaactgcga gaaaccaaag tcctttcccc                924
ccaaaggttc tgaaagcaaa caaaaaaaaa aaaaaaaaaa aaaaaaaaaa aaaaaaaaa                 984
aaaaaaaaaa aaaaaaaaaa gggcggccgc tctagagga                                      1023
```

```
<210> SEQ ID NO 4
<211> LENGTH: 207
<212> TYPE: PRT
<213> ORGANISM: Mus musculus

<400> SEQUENCE: 4

Met Tyr Ser Ala Pro Ser Ala Cys Thr Cys Leu Cys Leu His Phe Leu
1               5                   10                  15

Leu Leu Cys Phe Gln Val Gln Val Leu Ala Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Ala Glu Leu Gln Lys Pro Phe Lys Tyr Thr
            180                 185                 190

Thr Val Thr Lys Arg Ser Arg Arg Ile Arg Pro Thr His Pro Gly
        195                 200                 205

<210> SEQ ID NO 5
<211> LENGTH: 153
<212> TYPE: PRT
<213> ORGANISM: Homo sapien
```

```
<220> FEATURE:
<221> NAME/KEY: VARIANT
<222> LOCATION: 1
<223> OTHER INFORMATION: Xaa is Met or absent.

<400> SEQUENCE: 5

Xaa Arg Pro Ser Gly Arg Lys Ser Ser Lys Met Gln Ala Phe Arg Ile
 1               5                  10                  15

Trp Asp Val Asn Gln Lys Thr Phe Tyr Leu Arg Asn Asn Gln Leu Val
             20                  25                  30

Ala Gly Tyr Leu Gln Gly Pro Asn Val Asn Leu Glu Glu Lys Ile Asp
         35                  40                  45

Val Val Pro Ile Glu Pro His Ala Leu Phe Leu Gly Ile His Gly Gly
     50                  55                  60

Lys Met Cys Leu Ser Cys Val Lys Ser Gly Asp Glu Thr Arg Leu Gln
 65                  70                  75                  80

Leu Glu Ala Val Asn Ile Thr Asp Leu Ser Glu Asn Arg Lys Gln Asp
                 85                  90                  95

Lys Arg Phe Ala Phe Ile Arg Ser Asp Ser Gly Pro Thr Thr Ser Phe
             100                 105                 110

Glu Ser Ala Ala Cys Pro Gly Trp Phe Leu Cys Thr Ala Met Glu Ala
         115                 120                 125

Asp Gln Pro Val Ser Leu Thr Asn Met Pro Asp Glu Gly Val Met Val
     130                 135                 140

Thr Lys Phe Tyr Phe Gln Glu Asp Glu
145                 150
```